United States Patent [19]

Rea

[11] 4,062,937

[45] Dec. 13, 1977

[54] INSECT BITE RELIEF PREPARATION

[76] Inventor: La Verne Rea, 288 Broadway, Sp. 22, Chula Vista, Calif. 92010

[21] Appl. No.: 666,412

[22] Filed: Mar. 12, 1976

[51] Int. Cl.$^2$ .................. A61K 7/40; A61K 31/195
[52] U.S. Cl. .............................. 424/47; 424/DIG. 5; 424/319
[58] Field of Search ................. 424/319, DIG. 10, 47

[56] References Cited

U.S. PATENT DOCUMENTS

| 3,287,220 | 11/1966 | Martin | 424/319 X |
| 3,873,695 | 3/1975 | Pastre | 424/319 |
| 3,903,260 | 9/1975 | Beigler et al. | 424/319 |

FOREIGN PATENT DOCUMENTS

| 554,805 | 3/1938 | Canada | 424/319 |
| 2,040,954 | 1/1971 | France | 424/319 |
| 1,098,416 | 1/1968 | United Kingdom | 424/319 |

*Primary Examiner*—Dale R. Ore
*Attorney, Agent, or Firm*—Allen D. Brufsky

[57] ABSTRACT

An insect bite relief preparation that comprises an amino acid material in a suitable carrier for topical application to the skin in the area of an insect bite to relieve the discomfort thereof.

10 Claims, No Drawings

INSECT BITE RELIEF PREPARATION

BACKGROUND OF THE INVENTION

This invention relates to a topical skin preparation; more particularly, to an insect bite relief preparation that includes an amino acid material and a suitable carrier. The preparation finds particular utility in relieving the discomfort associated with bites and stings received from mosquitos, flies and similar insects.

The prior art teaches a variety of skin applications for bites as well as the voluminous art relating to amino acids, for example as disclosed in U.S. Pat. Nos. 1,471,344; 2,435,005; 3,061,512; 3,515,749; 3,666,863; 3,701,666; 3,825,664; 3,697,287; and others. None of the foregoing, however, teach the instant concept of treating the insect bite with an amino acid constituent so as to relieve the discomfort associated therewith.

SUMMARY OF THE INVENTION

It is accordingly an object of the instant invention to provide for an improved topical application for the relief associated with insect bites.

It is another object to provide for the same at relatively little cost thereby making it generally available.

These and other objects and advantages of the invention will become more apparent from the following detailed disclosure and claims.

Broadly speaking, the instant invention includes the provision of a topical skin preparation adapted to relieve the discomfort associated with insect bites comprising an effective amount of an alkali metal salt of glutamic acid in a suitably cosmetically acceptable vehicle therefor.

DETAILED DISCLOSURE

The essential active ingredient of the instant invention is an amino acid, more specifically papain which is a proteinase found in the juice of unripe papaya fruits. A less exotic name is glutamic acid, specifically the alkali metal glutamates. The foregoing is readily available in the market place and neither its method of preparation nor its documented physical and chemical properties are critical to this invention.

It has been found that the alkali metal salts of glutamic acid, specially, the non-toxic, non allergic mono salts thereof have particular utility; most specifically the sodium salt, e.g., mono sodium glutamate.

The exact mechanism or theory by which the instant invention works is not fully understood though it is believed that some degree of cellular breakdown is involved.

The essential active ingredient may be admixed with various adjuvants to form a variety of topical preparations. The glutamate is included in amounts of about 0.1 to 75% by weight, more particularly about 1-50%, more commonly about 1-25% by weight.

In preparing the various different physical forms of the invention any of the well known compounding and processing procedures well known in the art for preparation of the particular embodiment may be employed.

Similarly, any of the well known suitable components for such type preparations may be physically admixed therewith, generally in the amounts customarily used for such specific embodiments.

The propellant used in connection with the aerosol embodiment of the invention may be any non-toxic, liquifiable propellant suitable for use in connection with the dispensing of the material. That is to say, any non-toxic, volatile, organic material which exists as a gas at the temperature of use (and ambient or atmospheric pressure) and which exists as a liquid at the same temperature under superatmospheric pressures can be used as the gas-producing agent. Especially suitable are the $C_3$–$C_4$ aliphatic hydrocarbons, namely liquefied propane, n-butane, and isobutane; halogenated aliphatic hydrocarbons which contain from 1 to 2 carbon atoms and include, by way of example, methylene chloride, "Freons" such as dichlorodifluoromethane, monochlorodifluoromethane, dichlorotetrafluoroethane, trichlorofluoromethane, trichlorofluoroethane, difluoroethane, difluoromonochloroethane, trichlorotrifluoroethane, monofluorodichloroethane, pentafluoromonochloroethane; cyclic hexafluorodichlorobutane; octafluoropropane; and cyclic octafluorobutane; and mixtures of two or more thereof. Preferably the saturated hydrocarbons and halogenated saturated aliphatic hydrocarbons are employed in the subject composition. The boiling point of said propellant, or of the mixture of propellants, used in the final product should fall within the range of about −30° C. to about 50° C at atmospheric pressure. A highly desirable propellant for use in connection with the subject composition is a mixture of dichlorodifluoromethane and dichlorotetrafluoroethane in a 25:75 blend.

The propellant will normally constitute from about 65 to 97 percent of the final aerosol composition, preferably from about 80 to 93 percent by weight thereof in an aerosol embodiment.

The following examples are further illustrative of the nature of the present invention and it is to be understood that the invention is not limited thereto. All amounts therein as well as in the appended claims are by weight unless otherwise indicated.

EXAMPLE I

Aerosol Spray 0.1% to 10.0% Sodium Salt of Glutamic Acid
9.5 Perfume
To 100% - Ethanol (anhydrous, denatured)
40.0% Propellant - 12 (Fluorocarbon)

EXAMPLES 2 – 6

These examples illustrate the preparation of a liquid product which may be employed in a roll-on applicator.

| Ingredients | 2 | 3 | 4 | 5 | 6 |
|---|---|---|---|---|---|
| Na Salt of Glutamic Acid | 0.1 | 1.0 | 5.0 | 10.0 | 20.0 |
| Ethyl Alcohol | 17.5 | 17.5 | 17.5 | 17.5 | 17.5 |
| Surface-Active Agent | 1.0 | 1.0 | 1.0 | 1.0 | 1.0 |
| Gum | 0.65 | 0.65 | 0.65 | 0.65 | 0.65 |
| Allantoin | 0.1 | 0.1 | 0.1 | 0.1 | 0.1 |
| Glycerine | 3.0 | 3.0 | 3.0 | 3.0 | 3.0 |
| Water | Bal. | Bal. | Bal. | Bal. | Bal. |

The compositions are prepared by blending the ethyl alcohol (S.D. 40), perfume and surface-active agent (Igepal CO-630), aromatic polyethylene glycol ether, warming the mixture, and slowly adding gum (hydroxypropyl methylcellulose) where desired with stirring for a sufficient time to permit swelling of the gum to form a homogeneous solution. The major part of the water is then added and the remaining ingredients are added slowly in any desired order to the warmed solution with stirring.

EXAMPLE 7

A typical formulation for a cream is - Ingredients:

| Ingredients: | Percent |
|---|---|
| Na salt of Glutamic Acid | 25 |
| Glyceryl Monostearate | 11 | with the balance being primarily water, and small amounts of perfume, emollient materials, preservative, etc.

EXAMPLE 8

The following dry powder aerosol composition is prepared:

| | % by weight |
|---|---|
| Na Salt of Glutamic Acid | 6.0 |
| Isopropyl Palmitate | 0.5 |
| ("Bentone 38") Suspending Agent | 0.5 |
| Propylene Carbonate | 0.165 |
| Propellant - Dichlorodifluoromethane: Dichlorotetrafluoroethane (25:75) | 92.835 |

The aerosol suspension is prepared by first making a suspension concentrate. The concentrate is prepared by blending the "Bentone 38" with the isopropyl palmitate, the active ingredient and the propylene carbonate (wetting agent). The mixture is vigorously mixed at a temperature of about 20° C to form a gel. Some propellant is then added and the composition mixed to form a homogeneous concentrate mixture. The concentrate is then placed in a can, sealed with a suitable aerosol valve, and pressurized with the remainder of propellant. Finally, the aerosol container is shaken and a stable aerosol suspension thereby obtained.

EXAMPLE 9

A cream of the oil-in-water emulsion type is prepared having the following recipe, in which the parts are by weight:

| | Parts |
|---|---|
| Sorbitan monostearate (Span 60) | 5 |
| Polyoxyethylene sorbitan monostearate (Tween 60) | 2 |
| Beeswax | 10 |
| Anhydrous lanolin | 3 |
| Mineral oil | 20 |
| Peanut oil | 25 |
| Polyethylene glycol (molecular weight, 400) | 34 |
| Na Salt of Glutamic Acid | 33 |

In preparing the foregoing composition, the first four ingredients are melted and mixed together, after which the peanut oil and mineral oil are mixed in. The polyethylene glycol is added to the mixture with stirring at about 70° C., following which the mixture is cooled and the Na salt of glutamic acid is stirred in gently.

This composition when spread on the skin developed a sensible quantity of heat which produced a pleasant sensation of warmth. It is readily removable from the skin by means of tissue in the usual manner, and can also be removed by washing with water. In the latter case, some additional heat was developed, making it possible to employ cold water.

EXAMPLE 10 — LOTION

A lotion of the oil-in-water emulsion type is prepared having the following recipe, in which the parts are by weight:

| | Parts |
|---|---|
| Cetyl alcohol | 1 |
| Anhydrous lanolin | 2 |
| Stearic acid | 6 |
| Triethylene glycol | 186 |
| Na salt of glutamic acid | 78 |

The composition is prepared by melting and mixing the first three ingredients, after which the triethylene glycol is stirred in at about 70° C. The composition is cooled to room temperature, and the acid salt is stirred in.

EXAMPLE 11 — CREAM

A cream of the water-in-oil emulsion type is prepared having the following composition, in which the parts are by weight:

| | Parts |
|---|---|
| Beeswax | 10 |
| Anhydrous lanolin | 3 |
| Sorbitan monostearate (Span 60) | 1 |
| Mineral oil | 50 |
| Polyethylene glycol (molecular weight, 400) | 35 |
| Na salt of glutamic acid | 50 |

The composition is prepared by melting and mixing the first three ingredients, after which the mineral oil, then the polyethylene glycol are stirred in at about 70° C. Upon cooling to room temperature, the acid salt is gently stirred in.

EXAMPLE 12 — LIQUIFYING CREAM

A liquifying cream is prepared having the following composition, in which the parts are by weight:

| | Parts |
|---|---|
| Petrolatum | 15 |
| Liquid paraffin | 20 |
| Mineral oil | 65 |
| Na salt of glutamic acid | 30 |

The composition is prepared by melting and mixing the first three ingredients, after which the composition is cooled to approximately room temperature, and the acid salt is gently stirred in.

The composition can be employed in the same manner as conventional creams and is equally effective for the intended purpose.

EXAMPLE 13 — OINTMENT

A simple ointment is prepared having the following composition, in which the parts are by weight:

| | Parts |
|---|---|
| Polyethylene glycol (molecular weight, 400) | 50 |
| Polyethylene glycol (molecular weight, 4000) | 50 |
| Na salt of glutamic acid | 13 |

The composition is prepared by mixing the polyethylene glycols at a sufficiently high temperature to melt the high molecular weight material, after which the mixture is cooled to about room temperature and the acid salt is stirred in. Any of the usual skin conditioning or treating materials, medicaments, etc., may be added to the ointment as desired.

EXAMPLE 14 — BODY RUB

A body rub composition is prepared having the following recipe, in which the parts are by weight:

| | Parts |
|---|---|
| Sodium lauryl sulfate | 25 |
| Triethylene glycol | 75 |
| Polyethylene glycol (molecular weight, 6000) | 3 |
| Na salt of glutamic acid | 54 |

The composition is prepared by mixing the first three ingredients at a temperature high enough to melt the high molecular weight polyethylene glycol, after which the mixture is cooled to about room temperature and the acid salt is stirred in.

This body rub can be employed in the usual manner by first wetting the body then rubbing in the composition.

Creams can be of the usual white, emulsified or cold cream type, frequently referred to as the beeswax-borax type cream, or of the transluscent liquifying type, consisting of a mixture of hydrocarbon oils and waxes. The minimum basic ingredients required for a beeswax-borax emulsion type of cream are beeswax, mineral oil, borax and water. Spermaceti, cetyl alcohol, cocoa butter and vegetable oils can be incorporated as emollients. The transluscent liquifying type of cream will include a physical mixture of mineral oil, paraffin, petrolatum and other waxes. Emollient ingredients can also be incorporated in this type of cream.

The following are typical formulations for the beeswax-borax and liquifying cleansing creams contemplated by the invention:

| | Beeswax-borax, percent | Liquifying cleansing, percent |
|---|---|---|
| Beeswax | 8 | |
| Mineral oil | 39.0 | 54.5 |
| Paraffin | 7 | 20 |
| Cetyl alcohol | 1 | |
| Borax | 0.4 | |
| Water | 34.1 | |
| Petrolatum | 15 | 15 |
| Na salt of glutamic acid | 10.0 | 10.0 |

The following is a further example of a cleansing cream:

| | Percent |
|---|---|
| Beeswax | 9 |
| Paraffin | 10 |
| Mineral oil 65/75 | 25 |
| Cetyl alcohol | 1 |
| Deltyl Extra | 10 |
| Na salt of glutamic acid | 10.0 |
| Borax | 1 |
| Water | 32.5 |
| Perfume | 0.5 |

The following are examples of antimicrobial emollient creams:

| | Emollient creams, percent | |
|---|---|---|
| Part A: | | |
| Beeswax | 3.0 | 5.0 |
| Petrolatum | | 10.0 |
| Spermaceti | 3.0 | |
| Light mineral oil | 27.0 | 10.0 |
| Glyceryl monostearate, pure | 12.0 | 10.0 |
| Lanolin | | 22.0 |
| Propyl paraben | 0.15 | 0.15 |
| Na salt of glutamic acid | 5.0 | 10.0 |
| Part B: | | |
| Methyl paraben | | 0.15 |
| Water | | 32.4 |
| Perfume | | 0.3 |

The above formulations will serve as lotion emulsions upon dilution with more of the solvent base, water in the case of an oil-in-water lotion, and oily components in the case of a water-in-oil emulsion.

The conventional hand cream formulation is a modified vanishing cream of the oil-in-water type, the basic composition being a stearic acid soap as potassium stearate as the emulsifier, an excess of stearic acid, a humectant such as glycerol, and a high proportion of water. A hand lotion has a smaller proportion of solids, but is similar in formulation. Additional ingredients include barrier agents, emulsifiers, preservatives, perfume oils and coloring agents.

Stick formulations are made up to give the desired effect incorporated into a base which will disperse them uniformly and will flow smoothly when molten, such as vegetable and mineral oils, fatty esters and polyalkylene glycols. Waxes are used to strengthen the stick and raise the melting point. The following are typical examples of stick formulations incorporating Na salt of glutamic acid of the invention.

| | A, percent | B, percent |
|---|---|---|
| Beeswax | 13 | 15 |
| Ozokerite | | 10 |
| Carnauba wax | 8 | 5 |
| Ceresin wax | | 4 |
| Lanolin | 4 | 5 |
| Lanolin absorption base | | 14 |
| Isopropyl myristate | | 10 |
| Diethylsebacate | | 10 |
| Castor oil | 60 | 14 |
| Eosine | | 2 |
| Antioxidant | q.s. | q.s. |
| Perfume | q.s. | q.s. |

Although the foregoing specific examples represent typical recipes for a variety of cosmetic compositions, it will be understood that the identity and relative quantities of the several ingredients may be varied in accordance with conventional practice.

I claim:

1. A method of relieving the discomfort associated with an insect bite comprising topically applying to the area of the bite an effective amount of an alkali metal salt of glutamic acid in a cosmetically acceptable vehicle.

2. A method according to claim 1 in which the alkali metal salt is a mono salt.

3. The method according to claim 2 in which the salt is sodium.

4. A method according to claim 2 in which the vehicle is a dry powder.

5. A method according to claim 2 in which the vehicle is a cream.

6. A method according to claim 2 in which the vehicle is a lotion.

7. A method according to claim 2 in which the vehicle is an aerosol containing a non-toxic gas propellant which is liquifiable under superatmospheric pressure.

8. A method according to claim 7 in which the propellent is selected from the group consisting of alkanes having 3 or 4 carbon atoms, halogenated methane and mixtures thereof.

9. A method according to claim 2 in which the vehicle is a stick formulation containing waxes, said formulation flowing smoothly when melted.

10. A method according to claim 2 in which the vehicle is a liquid comprising ethyl alcohol, a surface active agent, a gum, allantoin, glycerine and water.

* * * * *